(12) United States Patent
Poggie et al.

(10) Patent No.: US 6,355,215 B1
(45) Date of Patent: Mar. 12, 2002

(54) WEAR-RESISTANT OLEFINIC MEDICAL IMPLANT AND THERMAL TREATMENT CONTAINER THEREFOR

(75) Inventors: Robert Poggie, Lake Hopatcong; Robert Averill, Ringwood; Richard Afflitto, Pompton Plains, all of NJ (US)

(73) Assignee: Implex Corp.

( * ) Notice: Subject to any disclaimer, the term of this patent is extended or adjusted under 35 U.S.C. 154(b) by 0 days.

(21) Appl. No.: 09/266,134

(22) Filed: Mar. 10, 1999

(51) Int. Cl.[7] ................................................ A61L 2/00
(52) U.S. Cl. .............................. 422/23; 422/21; 422/40; 422/186.04; 206/363; 206/524.3; 220/500
(58) Field of Search .............................. 422/22, 23, 40, 422/186.04; 522/65, 71, 161, 189; 220/500; 206/363, 524.3

(56) References Cited

U.S. PATENT DOCUMENTS

| | | | |
|---|---|---|---|
| 4,217,087 A | * | 8/1980 | Bowles .......................... 425/78 |
| 4,813,210 A | | 3/1989 | Masuda et al. |
| 5,037,928 A | * | 8/1991 | Li et al. ....................... 526/352 |
| 5,160,464 A | | 11/1992 | Ward et al. |
| 5,414,049 A | | 5/1995 | Sun et al. |
| 5,543,471 A | | 8/1996 | Sun et al. |
| 5,728,748 A | | 3/1998 | Sun et al. |
| 5,753,182 A | | 5/1998 | Higgins |

OTHER PUBLICATIONS

Poggie et al., Accelerated Aging and Associated Chenges in Ultra–High Molecular Weight Polyethylene (UHMW-PE)Microstructure as a Function of Resin Type and Consolidation Variables, *Standard Technical Publication,* 1987.

D.C. Sun et al, Material Property Comparison of Surgical Implant Grade UHMWPE and "Enhanced" UHMWPE, 1994.

* cited by examiner

*Primary Examiner*—Krisanne Thornton
(74) *Attorney, Agent, or Firm*—Duane Morris; Arthur L. Plevy (57) ABSTRACT

A prefabricated medical implant made of polymeric material having increased wear resistance without substantially changing its ductility and other physical properties is described. The implant is formed by a method including the steps of heating a sealed, packaged, prefabricated implant, having a reduced oxygen atmosphere, to an elevated temperature below its annealing point at a predetermined rate and held at that temperature for a predetermined time. After this time the packaged implant, while being maintained in a predetermined temperature range, is irradiated with a predetermined amount of gamma radiation. After irradiation, the implant is permitted to cool at a predetermined rate. Thermal conductive and thermal insulation containers are also provided for holding the packaged implants during the process.

32 Claims, 6 Drawing Sheets

WEAR-RESISTANT OLEFINIC MEDICAL IMPLANT AND THERMAL TREATMENT CONTAINER THEREFOR

FIELD OF THE INVENTION

This invention relates to medical implants with improved wear resistance, formed of a polymeric material such as ultra-high molecular weight polyethylene, a method for making the implants, and a container used to process the implants during thermal and radiation treatment.

BACKGROUND OF THE INVENTION

Various polymeric materials have been used for the preparation of orthopaedic total joint replacement devices. Among them, olefinic polymeric materials such as ultra-high molecular weight polyethylene (UHMWPE) are especially useful polymeric bearing materials because of their physical properties and in vivo compatibility. UHMWPE has been defined as a predominantly linear type polyethylene which has a relative viscosity of 2.3 or greater at a solution concentration of 0.05% at 135.degree. C. in decahydronaphthalene. The nominal weight average molecular weight between 400,000 to 10,000,000; more usually from three to six million.

Orthopaedic implants may be manufactured by machining UHMWPE raw material, supplied in the form of polymer rods and slabs, into the desired shape of the orthopaedic implant devices. Alternatively, the implant devices can be produced directly by compression molding of the UHMWPE polymer powder. After manufacture, the components go through a sterilization procedure, usually after being placed inside a sealed package made of impermeable materials.

Several sterilization methods may be used, such as ethylene oxide, heat, or radiation. Radiation treatment is preferred over ethylene oxide and heat treatment because ethylene oxide has toxicity concerns, and heating the manufactured implant beyond its annealing point can ruin it by altering its precise physical dimensions. Furthermore, heat can also destroy the integrity of the sealed package containing the implant. Suitable radiation methods include the use of x-ray, electron beam and gamma radiation to irradiate the implant according to standard sterilization criteria.

Unfortunately, high energy radiation of the type required for sterilization may destabilise the polymeric material, such as UHMWPE because of the generation of free radicals effected by radiation, especially in the presence of oxygen. If the implant is instead irradiated in an oxygen reduced, or oxygen free atmosphere, the radiation induced free radicals are reduced in concentration due to their reaction with neighboring free radicals to form carbon-carbon cross-links.

The prior art has recognized that the less the free radical concentration, the better the polymer material retains its physical properties over time. Conversely, the greater the free radical concentration, the greater the potential for physical properties of the implant to degrade over time. Several prior art patents and articles have reported methods which enhance UHMWPE physical properties by reducing free radical concentration. U.S. Pat. No. 5,037,928 titled "Process of Manufacturing Ultrahigh Molecular Weight Linear Polyethylene Shaped Articles" issued on Aug. 6, 1991 to S. Li, et al. discloses a prescribed heating and cooling process for preparing a UHMWPE exhibiting a combination of properties including a creep resistance of less than 1% without sacrificing tensile and flexural properties produced by a high compression process. U.S. Pat. No. 4,813,210 titled "Radiation-Sterilized Packaged Medical Device" issued on Mar. 21, 1989 to T. Masuda, et al. discloses a packaging method where a medical device which is sealed in a sterile bag, after radiation/sterilization, is hermetically sealed in an oxygen-impermeable material together with a deoxidizing agent for prevention of post-irradiation oxidation and additional free radical formation U.S. Pat. No. 5,160,464 titled "Polymer Irradiation" issued on Nov. 3, 1992 to I. M. Ward, et al. discloses a heating and irradiation process of oriented polyethylene having a weight average molecular weight less than or equal to 350,000 which produces improved strain rate sensitivity.

U.S. Pat. No. 5,414,049 titled "Non-oxidizing Polymeric Medical Implant" issued on May 9, 1995 to D. C. Sun, et al. discloses a method for heating, melting, and annealing UHMWPE raw material stock in an oxygen reduced atmosphere, to remove residual oxygen and moisture prior to forming the implant device. The forming process is also done under reduced oxygen atmosphere and the finished implant is later packaged in a sealed, air tight package. Afterwards, the packaged implant is irradiated with gamma radiation at ambient temperature, and then heat treated for several days in the absence of irradiation to cause free radicals to form self cross links without oxidation. At no time during the process does the temperature exceed the distortion temperature of the implants. For UHMWPE, the applicable processing temperature range is between about 25.degree. C. and about 140.degree. C.

Although the above referenced prior art methods may succeed in stabilizing the medical implant by reducing the free radical concentration, the additional cross linking caused by the irradiation and heating processes employed often cause a substantial change in implant physical properties, most notably a decrease in ductility (see e.g. D. C. Sun et al., Material Property Comparison of Surgical Implant Grade UHMWPE and "Enhanced" UHMWPE; 20$^{th}$ Annual Meeting of the Society for Biomaterials, Apr. 5–9, 1994, Boston, Mass.). The consequences of changes in physical properties, aside from the desirable increase in wear resistance, is largely unknown with respect to the function of the implant in vivo, and therefore should be avoided. One reason given is that a decrease in ductility and an increase in stiffness may concentrate stresses in a smaller volume of the implant, and perhaps lead to premature mechanical failure of the polyethylene implant.

SUMMARY OF THE INVENTION

The present invention relates to a prefabricated polymeric implant displaying a large increase in wear resistance while simultaneously showing minimal changes in ductility and other mechanical properties, and the process for producing the improved implant. The present invention also relates to containers used to process the packaged implants.

The improved implant, having previously been sealed in an impermeable package under a reduced oxygen atmosphere, is produced by the process comprising the steps of preheating the implant, without irradiation, to a predetermined temperature, followed by irradiation of the preheated implant with a predetermined quantity of electromagnetic radiation while the implant is maintained within a predetermined temperature range, and finally controlled cooling of the irradiated and heated implant at a predetermined rate; with the overall requirement that the temperature of the packaged, polymeric implant is never allowed to reach its annealing or thermal distortion temperature at any time during the process.

Thermal conductive and thermal insulation containers are also provided for holding the packaged implants during the above heating, irradiation, and cooling process steps. The thermal insulated container is adapted to hold the thermal conductive container and the thermal conductive container is adapted to hold at least one prefabricated implant in a sealed package.

For the purpose of illustration, UHMWPE will be used as an example to describe the invention. However, the inventive process should also apply to other polymeric materials such as polypropylene, high density polyethylene, polyester, nylon, polyurethane, poly(methylmethacrylate, and other polymeric materials capable of free radical formation when irradiated by gamma radiation in the 1.0 to 100.0 MRads range.

The thermal containers are so configured to facilitate the processing of the packaged implants, by obtaining the optimum heating, irradiation, and cooling for the packaged implants contained therein.

Preferred embodiments of the invention will be described below in the context of the medical implant made by the inventive process, the method of making the improved medical implant, and the thermal conductive and thermal insulation containers which are useful in the inventive process.

DESCRIPTION OF THE PREFERRED EMBODIMENTS

Figure 1:
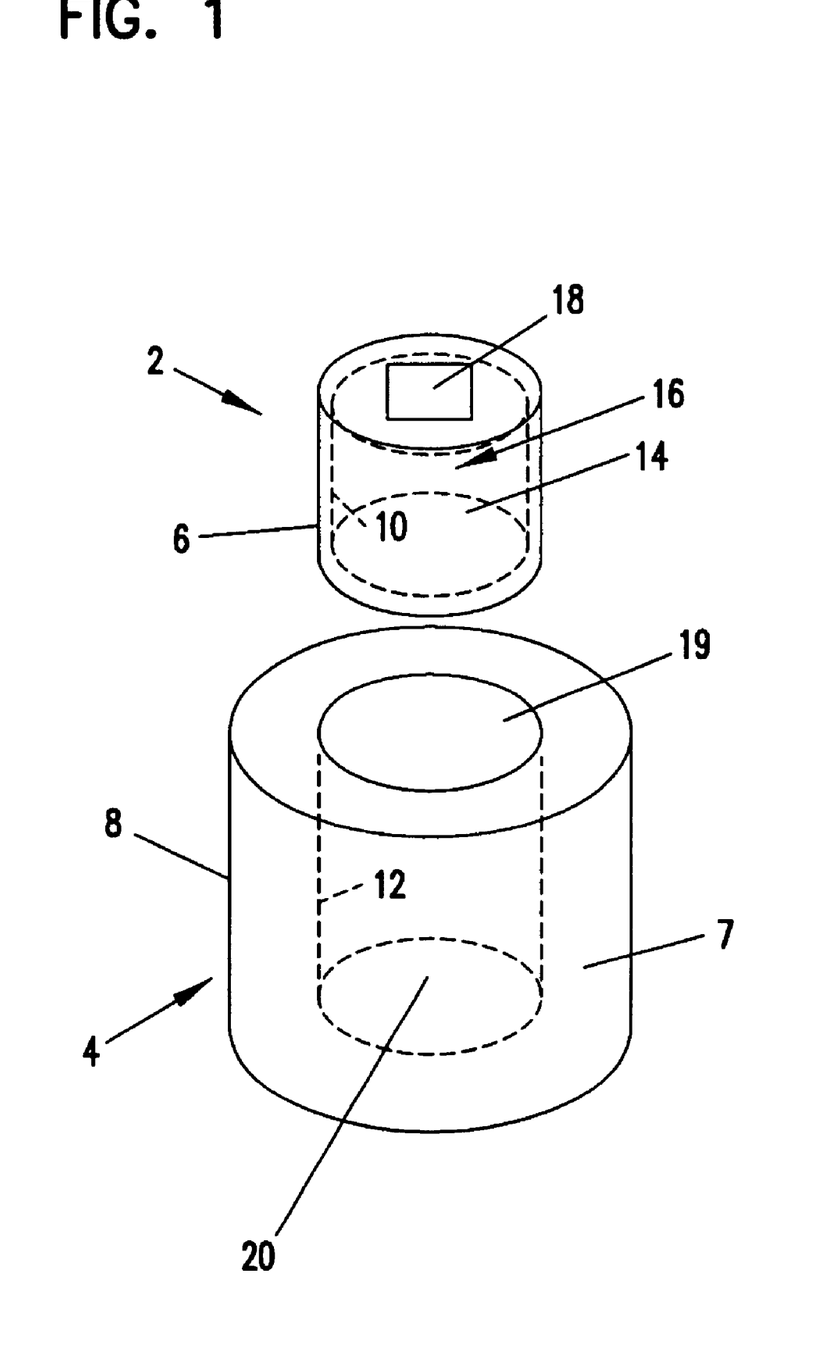
FIG. 1 is a perspective, exploded view of the thermal conductive container positioned to be received inside the thermal insulation container.

Referring to FIG. 1 there is shown an exploded view, in perspective format, of thermal conductive material having an inner chamber 2 with an exterior surface 6 and an interior surface 10. The interior surface 10 defines a space 14 adapted for holding an implant 16, which can be inserted through access means 18. Also shown is a thermal insulation material having an outer chamber 4 with a wall 7. The wall 7 has an exterior surface 8 and an interior surface 12. The interior surface 12 defines a space 20 adapted for holding inner chamber 2 which can be inserted into space 20 via access means 19.

Figure 2:
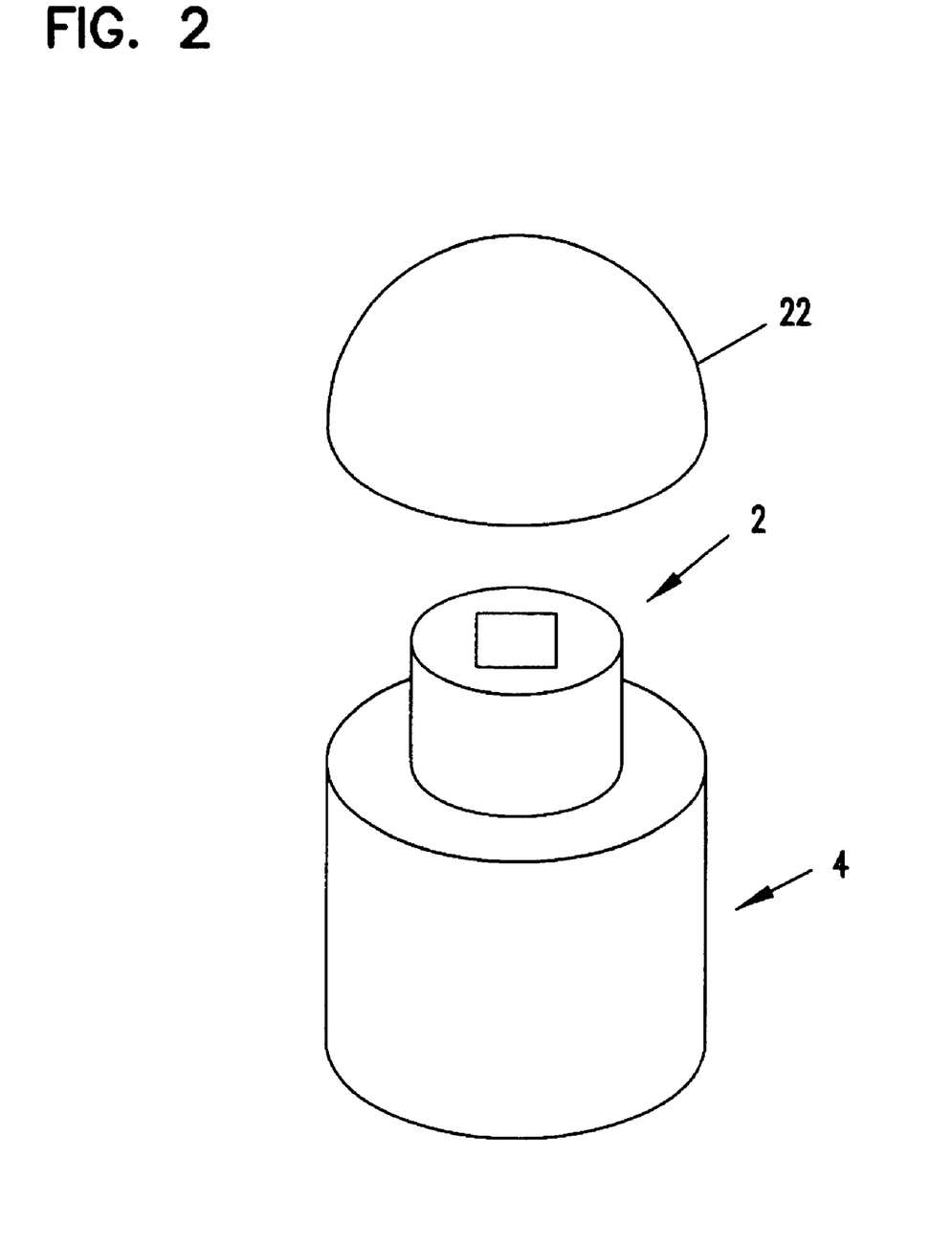
FIG. 2 is a perspective view of the thermal conductive container partially received inside the thermal insulation container and a lid for the thermal insulation container positioned to received onto the thermal insulation container.

Now referring to FIG. 2 there is shown a perspective view of inner chamber 2 being received into outer chamber 4. Lid 22 is shown in position to be received onto inner chamber 4 whereby inner chamber 2 would then be sealed inside outer chamber 4.

Figure 3A:
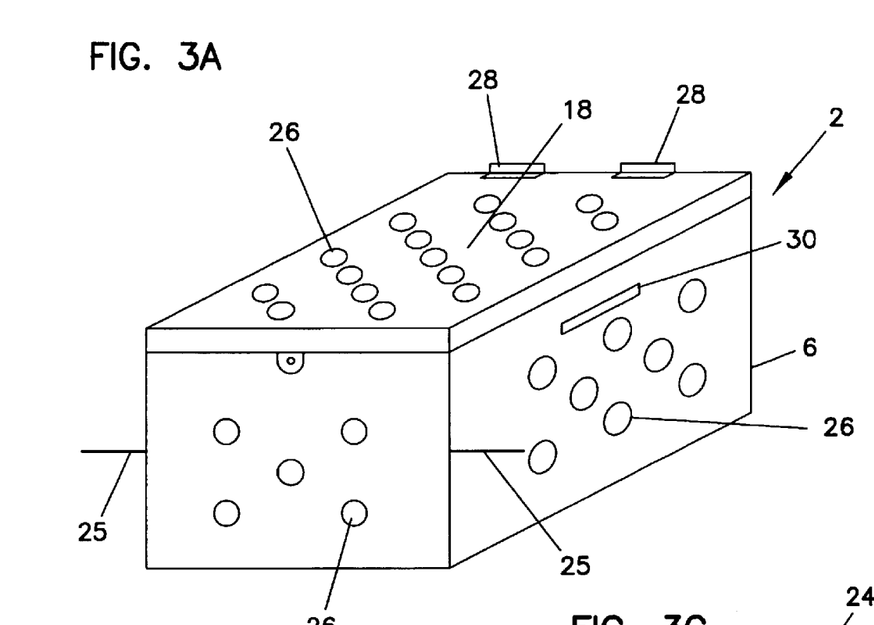
FIG. 3A is a perspective view of a preferred embodiment of a thermal conductive chamber of the present invention.

Now referring to FIG. 3A there is shown a perspective view of a preferred embodiment of inner chamber 2 having an access lid 18 with hinges 28, holes 26 for facilitating the circulation of heat (not shown), a handle 30, and axis 25.

Figure 3B:
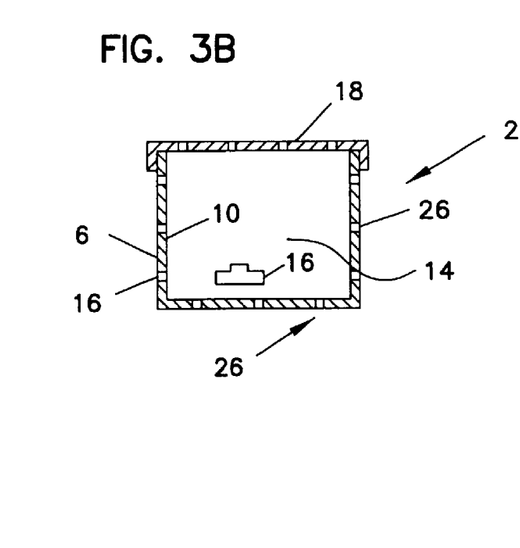
FIG. 3B is a cross sectional view of a sliced portion of the thermal chamber depicted in FIG. 3A along axis (25).

Now referring to FIG. 3B there is shown a cross-section view of a sliced portion of the inner chamber 2 along axis 25 as depicted in FIG. 3A. Also shown are holes 26, exterior surface 6 and an interior surface 10. The interior surface 10 defines a space 14 adapted for holding an implant 16, which can be inserted through access lid 18.

Figure 3C:
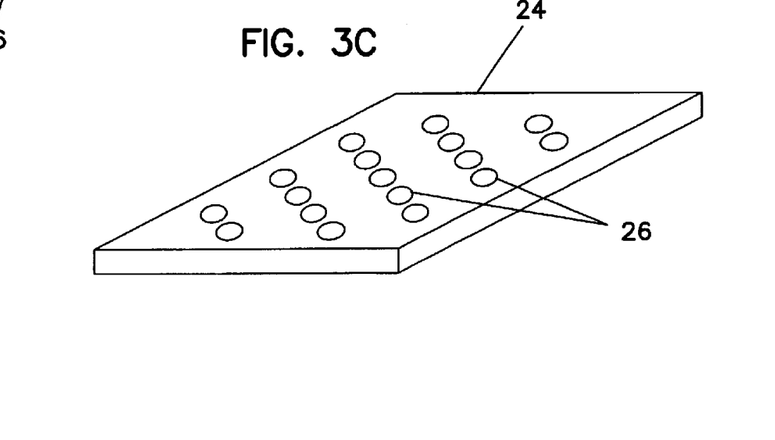
FIG. 3C is a perspective view of a thermal mass for optional use with the thermal chamber depicted in FIG. 3A.

Now referring to FIG. 3C there is shown a thermal mass 24 which may be used with inner chamber 2. Thermal mass 24 has one or more optional holes 26, and is sized for fitting either into inner chamber 2 or outer chamber 4 and adjacent to exterior surface 6.

Figure 4A:
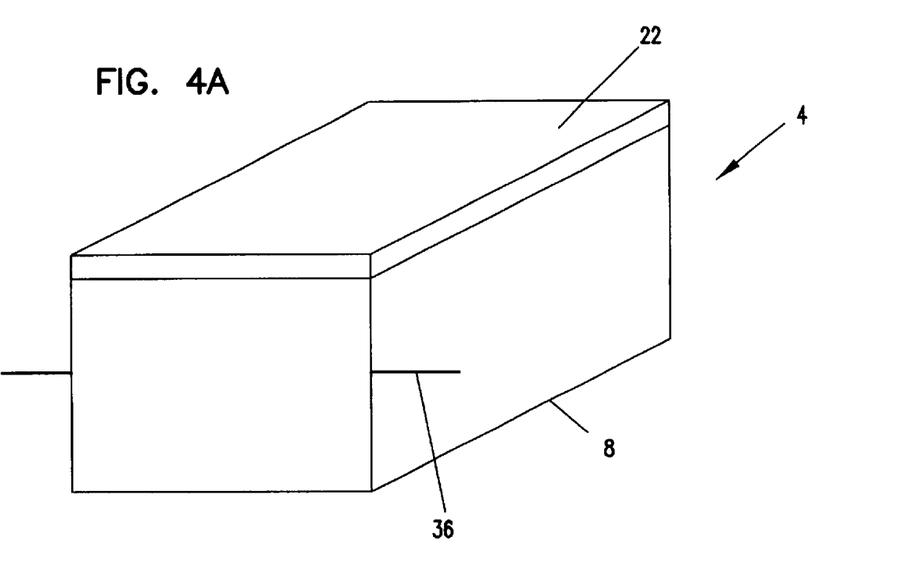
FIG. 4A is a perspective view of a preferred embodiment of a thermal insulation chamber of the present invention.

Now referring to FIG. 4A there is shown perspective view of a preferred embodiment of outer chamber 4 having a lid 22 covering an opening (not shown). Also shown is exterior surface 8, and axis 36.

Figure 4B:
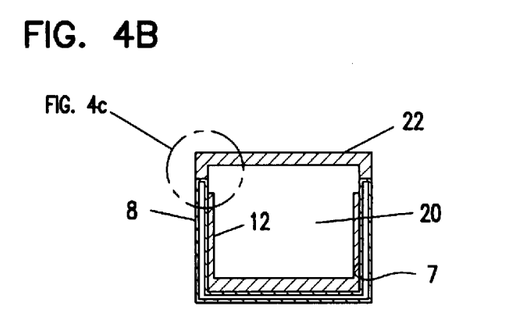
FIG. 4B is a cross sectional view of a sliced portion of the thermal chamber depicted in FIG. 4A along axis (36).

Now referring to FIG. 4B there is shown a cross-section view of a sliced portion of the outer chamber 4 along axis 36 as depicted in FIG. 4A. Also shown is lid 22, wall 7, exterior surface 8 and interior surface 12. The interior surface 12 defines a space 20 adapted for holding inner chamber 2, which can be inserted through opening (not shown) which lid 22 covers.

Figure 4C:
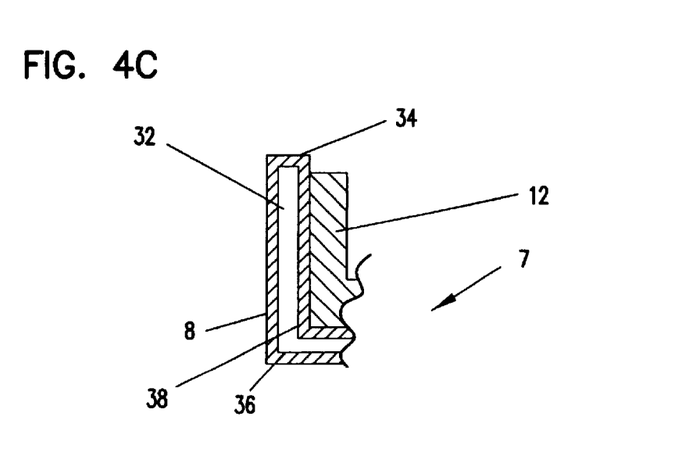
FIG. 4C is a sectional view of the sliced portion of the thermal insulation chamber depicted in FIG. 4B.

Now referring to FIG. 4C there is shown a section of the cross-section view of a sliced portion of the outer chamber 4 along axis 36 as depicted in FIG. 4A. Wall 7 is composed of interior surface 12 and exterior surface 8 both of which have thermal insulative ability. Exterior surface 8 is shown adjacent to a three layer laminate structure composed of a first layer 36, a second layer 38, an inner layer 32, and a seal 34.

In the inventive method, a raw polymeric material such as polypropylene, UHMWPE, polyester, nylon, polyurethane or poly(methylmethacrylate) is obtained for fabrication into a finished medical implant. UHMWPE is preferred due to its advantageous physical properties and compatibility in vivo. UHMWPE powder, pellets, bar stock or rod stock is obtained by, for example, ram extrusion, direct compression molding of parts, molding of sheet, or other forming processes. The implant is then either machined, or molded, or both molded and then machined to its intended configuration and packaged under a reduced oxygen or oxygen free atmosphere.

Suitable methods may be employed either alone or in combination, to reduce the oxygen content prior to sealing the implant in its package, e.g. purging with an inert gas, applying a vacuum, or a combination thereof. Suitable packaging materials for the implant treated by the inventive process include those that have the physical properties to withstand the stresses of shipping and handling, have little or no oxygen and moisture permeability, and transmit significant levels of electromagnetic radiation, e.g. x-ray, electron beam, and gamma radiation. Suitable packaging materials include foil laminates consisting of aluminum, polymers, and adhesive sealants, and the like. The packaging materials are selected to minimize or eliminate oxygen exposure of the implants during cross-linking or subsequent storage.

After the implant has been sealed in its package, it is heated to a predetermined temperature below its annealing or heat distortion temperature, for a predetermined amount of time, in the absence of electromagnetic radiation exposure. Suitable containers, such as inner chamber (2), for holding the implant during the heating process include those made of any thermally conductive material, such as aluminum, which can also efficiently transmit electromagnetic-radiation. The container will also conveniently have an access means (18) such as an opening and a lid (22) with hinges (28) for inserting the implant inside the container. The container will also optionally have one or more openings, such as holes (26) for facilitating heat transfer to the implants contained therein in a uniform and efficient manner, and handles (30) for ease of manipulation of the container. To promote implant heat retention, a material having a sufficient heat capacity may be optionally inserted inside the inner chamber (2) along with the implants, e.g. a thermal body (24) made out of mineral substance such as concrete, ceramic or a material with similar heat capacity. Thermal body (24) may consist of one or more separate sections, composed of the same or different materials. Alternatively, the thermal body (24) may be heated separately and brought in thermal contact with the implants at a later time. Thermal contact as used in this context means in sufficient proximity to transfer heat from a thermal body (24) or other device to the implants.

For UHMWPE, the annealing temperature is typically in the range of 95 to 110° C. Annealing is performed to stress relieve formed polyethylene shapes, and subsequent exposure of the polyethylene to a temperature equal to or in excess of its annealing temperature could cause distortion of the fabricated polyethylene forms.

In a preferred embodiment, the UHMWPE implant is heated to a temperature in the range of 60 to 110° C. with the range of to 73 to 88° C. being especially preferred. The time period that the implant is kept at this temperature is not critical, as long as the implant has sufficient time to come to thermal equilibrium prior to the next step in the process.

Next the preheated implant is irradiated with a predetermined quantity of electromagnetic radiation while the implant is held within a predetermined temperature range. For a UHMWPE implant, a preferred temperature range is 60 to 90° C. with the range of 73 to 88° C. being especially preferred. The temperature of the implant may be maintained during this step by any suitable method such as by placing the implant in a thermal insulation container during the irradiation process, such as outer chamber (4). Suitable thermal insulation containers will have an access means for inserting either the implants themselves, or a thermally conductive container containing the implants, e.g. an opening and a lid (22) adapted to sealing the opening. Furthermore, suitable thermal insulation containers will have walls (7) composed of materials or structures which inhibit heat flow, such as those with an R Factor (inches/btu) in the range of 1 to 10, and the like. The walls (7) may have simple or composite structures consisting of one or more of the following: insulation layers, laminate layers, gas filled or vacuum jacketed layers, and the like.

Some slight implant heating is usually observed during the irradiation process, and this heat gain can partially or wholly compensate for implant radiative heat loss so as to maintain the implant in the desired temperature range. Alternatively, the implant may be heated with a controlled heat source such as a thermostatically controlled heating/cooling device, and the like, during the irradiation step to maintain its temperature within the desired range.

Any electromagnetic radiation source of sufficient intensity for sterilization purposes may be used to irradiate the implants in the inventive process, such as x-ray, electron beam, or gamma radiation, and the like. Gamma radiation is especially preferred because of its wide commercial availability. A suitable radiation exposure range for UHMWPE implants is between 2.5 to 100.0 MRads, with a preferred range of 2.5 to 10.0 MRads, and an especially preferred range of 5.0 to 7.0 MRads.

Following the irradiation of the preheated implants, the implants are allowed to cool to ambient conditions (e.g. room temperature) at a predetermined rate. This is conveniently accomplished by placing the heated and irradiated implants in a thermally insulated box, such as outer chamber 4, which allows the implants to cool at a predetermined rate depending on the insulation ability of the materials which form the box. A preheated thermal body (24) may optionally be brought in thermal contact with the implants to help control the implants cooling rate. A suitable cooling rate range for UHMWPE implants is 0.005 to 1.0° C./ minute with a preferred range of 0.02 to 0.30° C./minute, and an especially preferred range of 0.03 to 0.20° C./ minute. Alternatively, the implant may be cooled by being placed in thermal contact with a controlled cooling source such as a thermostatically controlled heating/cooling device, and the like.

EXAMPLE 1

The effect of a preferred embodiment of the inventive process on implant wear resistance and other physical properties versus a comparative case was studied.

Two UHMWPE materials were prepared as follows: the materials were machined in the form of 28 mm acetabular liners, (Implex Corp.) from compression molded GUR 1020 sheet (Perplas Medical, Ltd.) which were subjected to gamma radiation sterilization within two evacuated foil packages (dual vacuum packaging). Material #1 was subjected to a typical sterilization dose of approximately 3 MRads (Comparative case). Material #2 (inventive case) was subjected to a radiation dose of about 6 MRads and processed as follows. Prior to irradiation, the inventive sample was placed in an aluminum thermal conductive container and preheated to 88° C. in a uniform manner. The sample was held at that temperature for approximately 6 hours in the absence of radiation. After receiving the 6 MRads of radiation, while being held within the temperature range of 65 to 88° C., the implant was then allowed to cool for 8 hours at an approximate cooling rate of 0.1° C./minute.

Hip wear simulation testing was performed with the 28 mm polyethylene liner inserts (n=5 for each of the two materials) in the anatomic position, using an eight station MTS machine (MTS Company). The liners were articulated with 28 mm Super-finished Co—Cr—Mo Femoral Heads (Ra<0.225 $\mu$m, available from Implex Corp.). Testing was conducted per the methods described in ASTM F-1714. Cycle rate was 1 Hz, load profile was Paul curve, maximum load was 3000 N (674 lbs.), the lubricant was Bovine calf serum supplemented with EDTA. Wear was assessed every 500,000 cycles using gravimetric methods; water absorption was measured and the wear rates corrected accordingly.
Results The results of the physical, mechanical, and swell ratio tests are listed in Table 1. The results indicate a significant increase in cross linking (as measured by a decrease in swell ratio) with the inventive process along with minimal change in ductility (as measured by % elongation). For comparative purposes, the swell ratio of virgin, non-irradiated GUR 1020 sheet (Perplas Ltd.) is approximately 20. Notwithstanding this change in swell ratio, comparison of the mechanical properties in Table 1 indicates that a change in radiation dose from about 3 to 6 MRads had minimal effect on mechanical properties in general, including Young's modulus which showed no statistically significant change.

TABLE 1

The mechanical and physical properties of ASTM F-648 polyethylene subjected to 3.0 MRads of gamma radiation (Comparative case,) and 6.0 MRads of gamma radiation (inventive process).

| Property | Comparative Material #1 | Inventive Material #2 |
|---|---|---|
| Yield strength (psi) | 3470 +/− 65 | 3650 +/− 35 |
| Ultimate strength (psi) | 6960 +/− 480 | 6660 +/− 400 |
| Young's modulus (psi) | 200 +/− 10 | 205 +/− 10 |
| % Elongation | 325 +/− 50 | 290 +/− 20 |
| IZOD impact (ft lb/in$^2$) | 59.8 +/− 43 | 51.3 +/− 7 |
| % Crystallinity | 58 | 60 |
| Density (g/cm3) | .9389 +/− .003 | .9423 +/− .003 |
| Oxidation Induction Temp. | 206 +/− 1.7 | 210 +/− 1.2 |
| Swell ratio | 5.3 | 3.1 |

Figure 5:
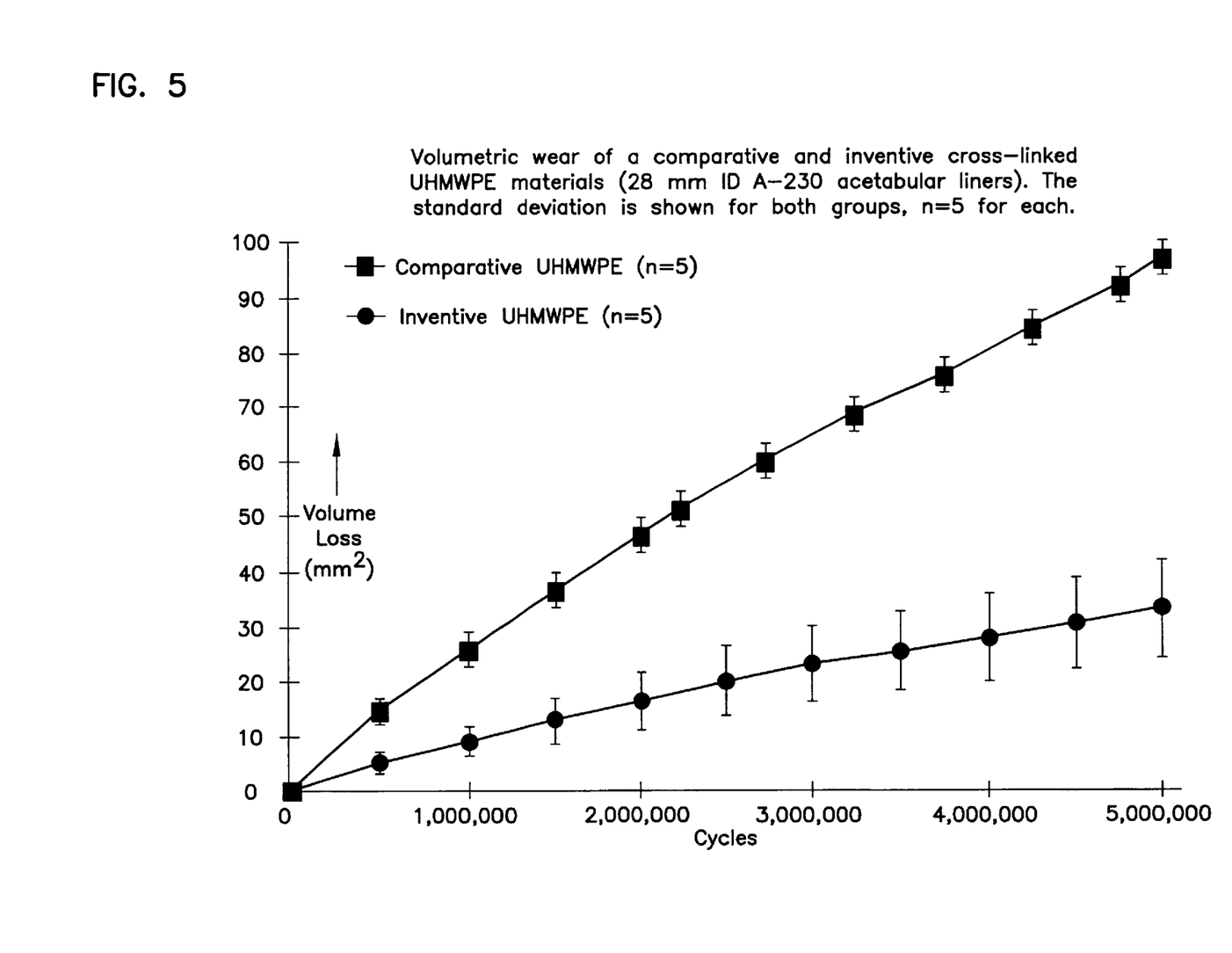
FIG. 5 is a graph comparing the wear resistance of 28 mm acetabular UHMWPE liners produced by a preferred embodiment of the inventive process with a comparative process.

The results of hip wear simulation testing are shown in FIG. 5 which demonstrates a 64% reduction in volumetric loss at 3 million cycles, and a projected similar decrease at 5 million cycles for the inventive process compared to the comparative process. The results of this wear test series further indicate that a substantial decrease in implant hip wear volume can be achieved by the inventive process. As mentioned above, the physical and mechanical properties data (see Table 1) indicate that this large reduction in implant acetabular wear can be achieved with no significant effect on ductility and other mechanical properties.

Oxidation Resistance Data

The oxidation resistance of the comparative and the inventive UHMWPE implants were determined using a standard accelerated oxidation method. The method involves the heating of. the UHMWPE samples to a temperature of 70° C. under a pure oxygen atmosphere, at five times atmospheric pressure for between 3 and 4 weeks. The duration of accelerated oxidation is determined by oxidation of control samples. The methodology is described in detail in an Implex Publication entitled "Accelerated Aging and Associated Changes in Ultra-High Molecular Weight Polyethylene (UHMWPE) Microstructure as a Function of Resin Type and Consolidation Variables". The results of the oxidation tests indicate that the inventive UHMWPE implant was at least as oxidation resistant as the comparative UHMWPE implant The reduced tendency for oxidation of the inventive UHMWPE implant is attributed to the fact that thermal processing during gamma radiation (pre-heat of 88° C.) causes cross-linking, which reduces the number of active molecules (free radicals) and thereby reduces oxidation potential.

EXAMPLE 2

The effect of the inventive process on wear resistance and other physical properties as a function of gamma radiation dosage compared to a comparative case was studied. Six UHMWPE materials were prepared as follows: All test samples originated from compression molded GUR 1020 sheet (Perplas Medical, Ltd.) which were later subjected to gamma radiation sterilization within two evacuated foil packages (dual vacuum packaging). The six materials were separated into two groups, an inventive and a comparative group. The comparative group being subjected to gamma radiation, and the inventive group being subjected to gamma radiation in conjunction with a preferred embodiment of the inventive process as described in Example 1. Subgroups of each of the above groups were separately subjected to 3, 6, and 9 MRads (low, medium, high dose) of gamma radiation. Mechanical testing was performed per ASTM D-638 (n=3) and swell ratio determined according to ASTM D-2765.

A preliminary series of hip wear simulation testing were performed with 28 mm polyethylene liner insets processed in each of the six conditions, with one sample per wear station. Testing was performed in the anatomic position, using an eight station MTS machine. The liners were articulated with 28 mm Co—Cr—Mo femoral heads (Ra<0.025 μm, Implex Corp.). Testing was conducted per the methods described in ASTM F-1714. Cycle rate as 1 Hz, load profile was a Paul curve, maximum load was 3000 N (674 lbs.), the lubricant was Bovine calf serum supplemented with EDTA. Wear was assessed to 1.8 million cycles, with the graph representing volumetric wear per million cycles.

Results

Figure 6:
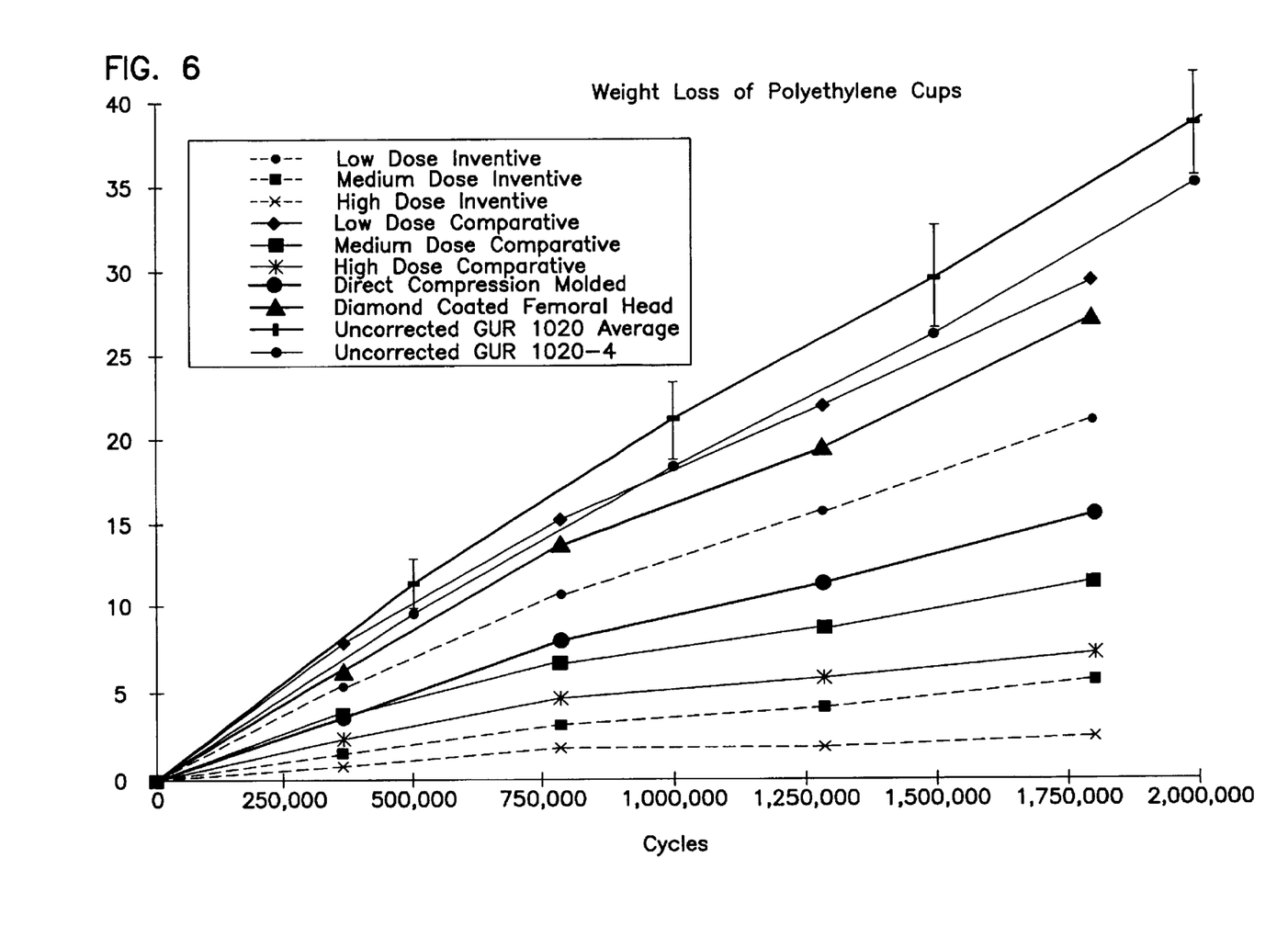
FIG. 6 is a graph comparing the wear resistance of 28 mm acetabular UHMWPE liners produced by another preferred embodiment of the inventive process with a comparative process as a function of gamma radiation exposure.

The results of the physical, mechanical, wear resistance (expressed as weight loss) and swell ratio tests are shown in Table 2. The results indicate a significant increase in wear resistance and cross linking (as measured by an observed decrease in swell ratio) for the samples treated by the inventive process. For comparative purposes, the swell ratio of virgin, non-irradiated GUR 1020 sheets (Perplas Ltd.) is approximately 20. The graph for acetabular liner wear is displayed in FIG. 6 as volume lost per million cycles, to a total of 1.8 million cycles.

TABLE 2

Effect of varying gamma radiation exposure on comparative and inventive sample properties.

| sample | gamma radiation exposure (MRads) | Elongation % | Yield strength % | Crystallinity % | Ultimate tensile strength % | Swell ratio | Wear resistance (mg) |
|---|---|---|---|---|---|---|---|
| comparative | 3 | 326 ± 52 (n = 21) | 3472 ± 65 (n = 21) | 58 | 6962 ± 480 (n = 21) | 5.21 ± .21 (n = 12) | 29.4 |
| comparative | 6 | 330 ± 10 (n = 3) | 3483 ± 25 (n = 3) | 60 | 7100 ± 321 (n = 3) | 4.0 ± .09 (n = 7) | 11.5 |

TABLE 2-continued

Effect of varying gamma radiation exposure on comparative and inventive sample properties.

| sample | gamma radiation exposure (MRads) | Elongation % | Yield strength % | Crystallinity % | Ultimate tensile strength % | Swell ratio | Wear resistance (mg) |
|---|---|---|---|---|---|---|---|
| comparative | 9 | 257 ± 12 (n = 3) | 3530 ± 30 (n = 3) | 63 | 6603 ± 372 (n = 3) | 3.3 ± .20 (n = 7) | 7.2 |
| inventive | 3 | 333 ± 25 (n = 3) | 3347 ± 87 (n = 3) | 59 | 6123 ± 871 (n = 3) | 3.8 ± .05 (n = 6) | 21.0 |
| inventive | 6 | 287 ± 18 (n = 10) | 3547 ± 35 (n = 10) | 60 | 6658 ± 404 (n = 10) | 3.1 ± .051 (n = 7) | 5.8 |
| inventive | 9 | 233 ± 12 (n = 3) | 3457 ± 42 (n = 3) | 60 | 6200 ± 440 (n = 3) | 2.3 ± .22 (n = 6) | 2.6 |

Based on the results from Table 2, it can be seen that the comparative case (i.e. gamma radiation without preheating) and the inventive process were both effective in promoting cross-linking, as indicated by the swell ratio data. Furthermore, a decreasing swell ratio demonstrated a trend of decreasing hip wear. The mechanical properties data suggests a steady decrease in ductility with increasing cross-linking, and a peak in the UTS at about 6 MRads. Yield strength increased slightly as gamma dose increased. The results of these tests indicate that gamma radiation in doses (e.g. 6 to 9 MRads) moderately above those commonly used to sterilize implants today (e.g. 2.5 to 4.0 MRads) can be highly effective in reducing acetabular liner wear, and the inventive process further cross-links UHMWPE and reduces wear without substantially changing ductility and other mechanical properties.

While several examples of the present invention have been described, it is obvious that many changes and modifications may be made thereunto, without departing from the spirit and scope of the invention.

We claim:

1. A medical implant having increased wear resistance composed of a polymeric material, said implant having been sealed in a package having a reduced oxygen atmosphere, produced by the process comprising the steps of:
   heating said implant, in the absence of radiation, to a predetermined elevated temperature for a predetermined time interval;
   irradiating said preheated implant with a predetermined quantity of radiation while said implant is maintained within a predetermined elevated temperature range during said irradiation exposure; and
   cooling the implant at a predetermined cooling rate, in the absence of said radiation.

2. The medical implant as set forth in claim 1 wherein said polymeric material is polyethylene having a molecular weight of between about 1.0 and 6.0 million.

3. The medical implant of claim 1 wherein said reduced oxygen atmosphere comprises an inert gas, a vacuum, or a combination thereof, and contains no more than about 1.0% of oxygen (volume/volume).

4. The medical implant of claim 1 wherein said elevated temperature is between about 60 and 90° C.

5. The medical implant of claim 1 wherein said radiation is gamma radiation in the range of about 2.5 MRads to 100.0 MRads.

6. The medical implant of claim 1 wherein said radiation is gamma radiation in the range of about 2.5 MRads to 10.0 MRads.

7. The medical implant of claim 1 wherein said radiation is gamma radiation in the range of about 5.0 MRads to 7.0 MRads.

8. The medical implant of claim 1 wherein said predetermined time interval for holding said implant at said elevated temperature is in the range of about 1 hour to 100 hours.

9. The medical implant of claim 1 wherein said predetermined temperature range is about 65 to 88° C.

10. The medical implant of claim 1 wherein said predetermined cooling rate is in the range of about 0.005° C./minute to 1.0° C./minute.

11. A method for producing a prefabricated medical implant having increased wear resistance composed of a polymeric material having been sealed in a package having a reduced oxygen atmosphere, comprising the steps of:
    heating said packaged implant, in the absence of radiation to a predetermined elevated temperature for a predetermined time interval;
    irradiation said implant with a predetermined quantity of radiation while said implant is maintained within a predetermined elevated temperature range during said irradiation exposure; and
    cooling the implant at a predetermined cooling rate, in the absence of said radiation.

12. The method as set forth in claim 11 wherein said polymeric material is polyethylene having a molecular weight of between about 1 and 6 million.

13. The method as set forth in claim 11 wherein said reduced oxygen atmosphere comprises an inert gas, a vacuum, or a combination thereof, and contains no more than about 1% of oxygen (volume/volume).

14. The method as set forth in claim 11 wherein said elevated temperature is between about 60 and 90° C.

15. The method as set forth in claim 11 wherein said radiation is gamma radiation in the range of about 2.5 MRads to 100.0 MRads.

16. The method as set forth in claim 11 wherein said radiation is gamma radiation in the range of about 2.5 MRads to 10.0 MRads.

17. The method as set forth in claim 11 wherein said radiation is gamma radiation in the range of about 5.0 MRads to 7.0 MRads.

18. The method as set forth in claim 11 wherein said predetermined temperature range is about 60 to 90° C.

19. The method as set forth in claim 11 wherein said predetermined time interval for holding said implant at said elevated temperature is in the range of about 1 hour to 100 hours.

20. The method as set forth in claim 11 wherein said predetermined cooling rate is in the range of about 0.005° C./minute to 1.0° C./minute.

21. A thermal treatment containment apparatus for treating at least one packaged, prefabricated medical implant composed of a polymeric material, comprising:

a thermal conductive material in the form of an inner chamber and a thermal insulation material in the form of an outer chamber; each chamber having an exterior surface, and an interior surface;

said inner chamber's interior surface defining a space adapted for holding at least one of said implant, said inner chamber having at least one access means through which said implant is inserted into the space of said inner chamber;

said thermal conductive material having the properties to transmit gamma radiation and heat to the implant contained therein such that said implant will receive a predetermined dose of said radiation and reach a predetermined temperature;

said outer chamber's interior surface defining a space adapted for holding said inner chamber; and said thermal insulation material having the properties to control the transfer of heat away from said inner chamber wherein the implant contained therein will cool at a predetermined cooling rate.

22. The thermal treatment containment apparatus of claim 21 wherein said predetermined dose of radiation is gamma radiation in the range of about 2.5 MRads to 100.0 MRads.

23. The thermal treatment containment apparatus of claim 21 wherein said predetermined elevated temperature is in the range of about 60 to 90° C.

24. The thermal treatment containment apparatus of claim 21 wherein said predetermined time is in the range of about 1 to 100 hours.

25. The thermal treatment containment apparatus of claim 21 wherein said predetermined cooling rate is in the range of about 0.005° C./minute to 1.0° C./minute.

26. The thermal treatment containment apparatus of claim 21 wherein said thermal conductive material contains one or more holes for circulating heat uniformly to said implants.

27. The thermal treatment containment apparatus of claim 21 wherein said thermal conductive material is aluminum.

28. The thermal treatment containment apparatus of claim 21 wherein said inner chamber is in thermal contact with a thermal mass body.

29. The thermal treatment containment apparatus of claim 21 wherein said thermal insulation material is composed of one or more layers of materials each having an R Factor in the range of about 1 to 10 (inches/Btu).

30. The thermal treatment containment apparatus of claim 21 wherein said thermal insulation material has a wall which contains a layer which is sealed and evacuated.

31. The thermal treatment containment apparatus of claim 21 wherein said thermal insulation material has a wall which contains a layer which is sealed and filled with a gas.

32. A method for producing a prefabricated medical implant having increased wear resistance composed of a polymeric material, having been sealed in a package having a reduced oxygen atmosphere, comprising the steps of:

positioning said package implant into a thermal treatment containment apparatus composed of a thermal conductive material in the form of an inner chamber having an interior surface and an exterior surface;

said inner chamber's interior surface defining a space adapted for holding at least one of said implants, said inner chamber having at least one access means through which said implant is inserted into the space of said inner chamber;

said thermal conductive material being capable of transmitting both gamma radiation and heat to the implant contained therein such that said implant will receive a predetermined dose of said radiation and reach a predetermined elevated temperature;

heating said implant, in the absence of radiation to a predetermined elevated temperature for a predetermined time interval;

irradiating said implant with a predetermined quantity of radiation while said implant is maintained within a predetermined temperature range during said irradiation exposure;

positioning said inner chamber into an outer chamber having an interior surface defining a space adapted for holding said inner chamber after irradiating said implant;

said outer chamber being composed of a thermal insulation material being capable of transferring heat away from said inner chamber wherein the implant will cool at a predetermined cooling rate; and cooling the implant at said predetermined cooling rate, in the absence of said radiation.

* * * * *